US012797539B2

(12) United States Patent
Kuehn et al.

(10) Patent No.: US 12,797,539 B2
(45) Date of Patent: Nov. 17, 2026

(54) WEARABLE INJECTION DEVICE

(71) Applicant: Sanofi, Paris (FR)

(72) Inventors: Bernd Kuehn, Frankfurt am Main (DE); Florian Schauderna, Frankfurt am Main (DE)

(73) Assignee: Sanofi, Paris (FR)

( * ) Notice: Subject to any disclaimer, the term of this patent is extended or adjusted under 35 U.S.C. 154(b) by 860 days.

(21) Appl. No.: 17/926,290

(22) PCT Filed: May 19, 2021

(86) PCT No.: PCT/EP2021/063260
§ 371 (c)(1),
(2) Date: Nov. 18, 2022

(87) PCT Pub. No.: WO2021/233982
PCT Pub. Date: Nov. 25, 2021

(65) Prior Publication Data

US 2023/0211082 A1 Jul. 6, 2023

(30) Foreign Application Priority Data

May 20, 2020 (EP) .................................... 20315251

(51) Int. Cl.
*A61M 5/172* (2006.01)
*A61M 5/142* (2006.01)
(Continued)

(52) U.S. Cl.
CPC ...... *A61M 5/1723* (2013.01); *A61M 5/14248* (2013.01); *A61M 5/148* (2013.01);
(Continued)

(58) Field of Classification Search
CPC ............ A61M 5/1723; A61M 5/14248; A61M 5/148; A61M 5/16804; A61M 2202/0486;
(Continued)

(56) References Cited

U.S. PATENT DOCUMENTS 4,734,092 A 3/1988 Millerd
11,229,738 B2 * 1/2022 Møller .............. A61M 5/14244
(Continued)

FOREIGN PATENT DOCUMENTS

JP 2013-503692 A 2/2013
JP 2020-507457 A 3/2020
WO 2011/028279 A1 3/2011

OTHER PUBLICATIONS

International Search Report and Written Opinion for Application No. PCT/EP2021/063260, dated Jun. 2, 2021 and mailed on Jun. 11, 2021, 9 pages.

(Continued)

*Primary Examiner* — Courtney D Heinle
*Assistant Examiner* — Andrew Thanh Bui
(74) *Attorney, Agent, or Firm* — McCarter & English, LLP

(57) ABSTRACT

The present disclosure relates to wearable injection devices that comprise flexible elements. Exemplary devices can comprise flexible reservoirs, flexible housings, and flexible metering mechanisms. The flexible elements of the present disclosure provide improved wearable injection devices with small heights, low profiles, and streamlined, flexible cases that can withstand impact without experiencing adverse performance effects or tearing off of the patient.

14 Claims, 7 Drawing Sheets

(51) Int. Cl.
*A61M 5/148* (2006.01)
*A61M 5/168* (2006.01)

(52) U.S. Cl.
CPC . *A61M 5/16804* (2013.01); *A61M 2202/0486* (2013.01); *A61M 2205/3569* (2013.01); *A61M 2205/8206* (2013.01)

(58) Field of Classification Search
CPC .. A61M 2205/3569; A61M 2205/8206; A61M 2005/14252; A61M 2005/1583; A61M 5/14244; A61B 5/14532; A61B 5/14542
See application file for complete search history.

(56) References Cited

U.S. PATENT DOCUMENTS

| | | | |
|---|---|---|---|
| 2011/0054285 | A1 | 3/2011 | Searle et al. |
| 2019/0298921 | A1 | 10/2019 | Stafford |
| 2021/0252256 | A1 * | 8/2021 | Berenson .......... A61F 13/00063 |

OTHER PUBLICATIONS

Japanese Office Action for Application No. 2022-570277, dated Oct. 29, 2024, 8 pages.

* cited by examiner

WEARABLE INJECTION DEVICE

CROSS-REFERENCE TO RELATED APPLICATIONS

This application is a 35 U.S.C. § 371 national stage filing of International Application No. PCT/EP2021/063260 filed on May 19, 2021, which in turn claims priority to European Patent Application No. 20315251.7, filed May 20, 2020. The entire contents of each of the foregoing applications are included herein by reference in their entirety.

The present disclosure relates generally to wearable injection devices, such as patch pumps and pump systems, having flexible elements. The wearable injection device enables parenteral routes of administration such as subcutaneous, intradermal, intramuscular, or intravenous delivery.

Common diseases that require frequent injections can be burdensome to patients. For example, diabetes patients must monitor and adjust blood glucose levels at multiple times per day by administering insulin injections. Other therapies, like treating chronic pain, migraine, rheumatoid arthritis, psoriasis, IBD/Crohn's, asthma, dermatitis, cardio-vascular disorders, or treating cancer with immuno-oncology drugs may require frequent injections and delivery of larger volumes of more than 2 mL per injection. These measures can interrupt a patient's daily routine and adversely affect their lifestyle.

Presently, there are two types of wearable injection devices that are used by patients who require frequent parenteral injections. The first is an injection pump worn off of the body, usually on a belt. Tubing connects the pump to a needle inserted into the body. The second, relating to the present disclosure, is a patch pump that is attached to a patient's skin using adhesives. Patch pumps can provide partially automated medicament injection and alleviate some of the burdens facing patients. However, there can be drawbacks to existing patch pumps.

For example, patch pumps that initially served a patient for between a few hours and one day have now been adapted to last three days or more. As the need for longer lasting patch pumps has risen, conventional reservoirs and batteries used in patch pumps grew in size to meet this need and resulted in pumps with increased weight, and larger heights extending further from the patient's skin. Additionally, existing patch pumps have rigid cases that cannot deform with the skin during patient movement. Also, existing patch pumps require a relatively strong pump mechanism to overcome the break loose and glide forces of stoppers that are present in conventional reservoirs; this further adds to the size of the pump mechanism and the battery. For these reasons, existing patch pumps can dislodge or move when a patient bumps into a rigid body. Patch pumps have the potential to help alleviate the burdens of patients with diseases that require frequent injections. However, the shortcomings of presently available patch pumps have slowed their adoption.

There is a need for improved patch pumps that overcome the drawbacks of currently available devices. Accordingly, the present disclosure relates to wearable injection devices, such as patch pumps and patch pump systems, with flexible bodies and flexible reservoirs, which provide advantages over existing devices.

SUMMARY

The present disclosure relates generally to wearable injection devices with flexible elements that provide improved user experience and quality of care. The wearable injection devices can include multiple flexible elements such as a flexible housing, flexible reservoir, and flexible electronics. The flexible elements can decrease the profile of the device and allow the device to bend and flex with the skin of the patient on which it is adhered. This can reduce patient discomfort and minimize the chances of an abrupt dislodgement of the device that can occur when a patient is engaging in physical activity, to which e.g. diabetes patients are encouraged for improving their state of health.

In one embodiment, the present disclosure provides a wearable injection device comprising a housing that comprises a flexible body and a reservoir. The reservoir comprises a flexible outer wall with an inner volume and at least one port in fluid communication with the inner volume. In various embodiments, the flexible body comprises one of silicone, polyurethane rubber, or synthetic rubbers, such as neoprene foam, styrene-butadiene rubber (SBR), styrene-chloroprene rubber (SCR) or chloroprene rubber (CR).

The wearable injection device of the present disclosure further includes a pump mechanism configured to dispense a medicament from the wearable injection device. In various embodiments, the wearable injection device further includes an injection mechanism in fluid communication with the inner volume of the reservoir. Further, the wearable injection device includes a metering mechanism configured to control a dosage of the medicament dispensed from the wearable injection device.

In another embodiment, the present disclosure provides a wearable injection device including a housing that includes plates and a reservoir. The reservoir includes a flexible outer wall with an inner volume and at least one port in fluid communication with the inner volume. The wearable injection device further includes a pump mechanism configured to dispense a medicament from the wearable injection device. In various embodiments, the wearable injection device further includes an injection mechanism in fluid communication with the inner volume of the reservoir. Further, the wearable injection device includes a metering mechanism configured to control a dosage of the medicament dispensed from the wearable injection device.

In another embodiment, the present disclosure provides methods of delivering medicament including attaching a wearable injection device to a user and powering the wearable device. The method of delivering a medicament further includes sending a signal to the metering mechanism and dispensing a medicament at a programmable dosage and frequency. In some embodiments, the method further includes bending or compressing the wearable injection device without permanently affecting the performance and function of the wearable injection device.

In various embodiments, the medicament used in the devices and methods of the present disclosure is insulin. In some embodiments, the medicament includes one of a human insulin, a human insulin analogue or derivative, a glucagon-like peptide (GLP-1), a GLP-1 analogue, a GLP-1 receptor agonists, a GLP-1 analogue or derivative, a dipeptidyl peptidase-4 (DPP4) inhibitor, a pharmaceutically acceptable DPP4 salt, a DPP4 solvate, or any mixture thereof.

In another embodiment, the present disclosure provides a reservoir used in an injection device. The reservoir includes a flexible outer wall, an inner volume, at least one port, and a channel connecting the at least one port with the inner volume. In some embodiments, the flexible outer wall of the reservoir includes one a polymer. In some embodiments, the at least one port includes a resealable membrane or valve.

The embodiments of the present disclosure provide wearable injection devices, such as patch pumps, and methods of delivering medicaments that improve user experience and quality of care. The embodiments of the present disclosure provide flexible elements that can lower the profile of the device. The disclosed embodiments also provide wearable injection devices that can bend and flex with the skin on which they are adhered to reduce patient discomfort and prevent dislodgement of the device.

BRIEF DESCRIPTION OF THE DRAWINGS

Reference will now be made to exemplary embodiments, examples of which are illustrated in the accompanying drawings. Wherever possible, the same reference numbers will be used throughout the drawings to refer to the same or like parts. The drawings are not necessarily to scale.

DETAILED DESCRIPTION OF EXEMPLARY EMBODIMENTS

Figure 1:
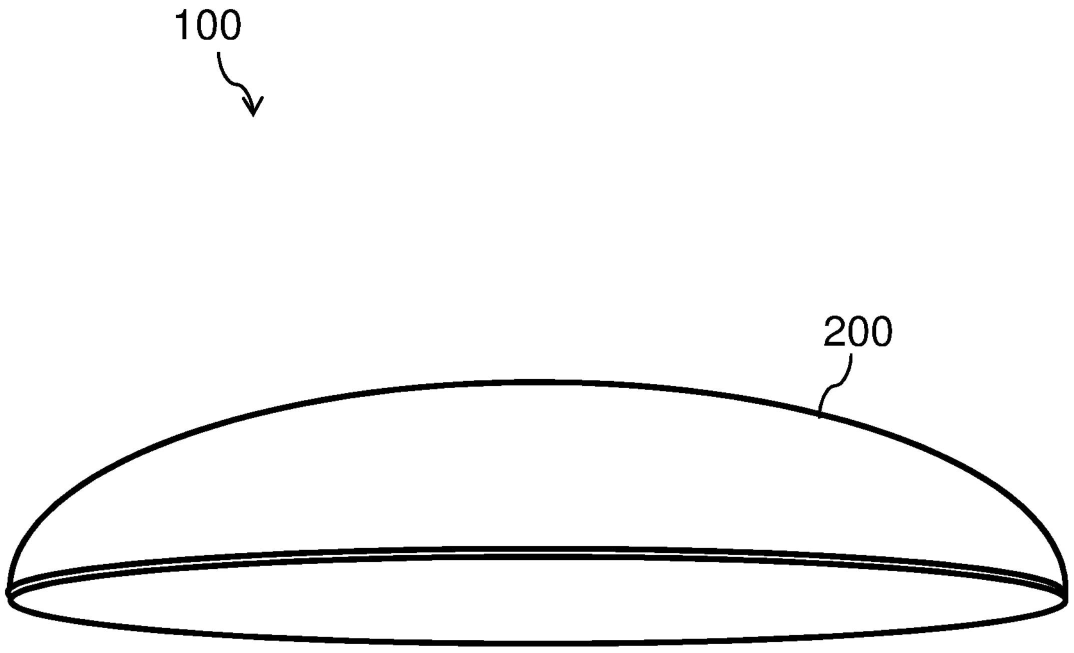
FIG. 1 illustrates a wearable injection device, according to various embodiments of the present disclosure.

Reference will now be made in detail to various embodiments of the disclosed devices and methods, examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including" as well as other forms, such as "includes" and "included," is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Existing patch pumps that are adhered to a patient's skin provide partially automated drug injection, alleviating some of the burden for patients. However, there are drawbacks to existing patch pumps. For example, as the need for longer lasting patch pumps has risen, conventional reservoirs and batteries used in patch pumps have grown in size and resulted in pumps with larger heights and weight that extend further from the patient's skin. Existing patch pumps can pull the adhesive from the skin and lead to loosening of the device from the patient's skin. These drawbacks have prevented the development of patch pumps for a wider range of therapeutic indications, such as those where larger volumes must be administered over the course of several days.

Additionally, existing patch pumps have rigid cases that cannot deform during human movement with the skin or limb to which is it attached. For this reason, existing patch pumps can tear off when a patient bumps into a rigid body. For example, existing patch pumps can tear off when a patient bumps into a doorframe or similar hard surface. Patch pumps have the potential to help alleviate the burden of monitoring and regulating glucose levels for millions of diabetes patients. However, the shortcomings of presently available patch pumps have slowed their adoption.

Furthermore, existing patch pumps are using conventional reservoirs where the pump mechanism needs to move a rubber stopper to expel the drug. This movement requires the pump mechanism to overcome a break loose and a glide force, which can be relatively high, having certain variability, and may increase with storage time. Therefore, the pump mechanism and the battery in existing patch pumps need to be dimensioned adequately to cope with the break loose and a glide forces present in conventional reservoirs. In the proposed embodiment with a flexible container, these forces are not present, allowing the implementation of a smaller pump mechanism and smaller batteries, which can result in smaller injection devices, lighter devices, and/or devices with lower profiles.

Embodiments of the present disclosure relate to wearable injection devices, such as insulin patch pumps, comprising flexible elements. The flexible elements of the present disclosure result in wearable injection devices that have lower profiles and less weight than existing devices. Additionally, wearable injection devices of the present disclosure comprise a flexible body that can flex and twist with the patient. The wearable injection devices of the present disclosure move more naturally with the patient, increasing patient comfort and reducing the risk of dislodgement or loosening.

One embodiment of an exemplary wearable injection device, injection device 100, is shown in FIG. 1. As shown, injection device 100 comprises housing 200. Injection device 100 and its components are described in greater detail in FIG. 2, which illustrates an exploded view of injection device 100.

Figure 2:
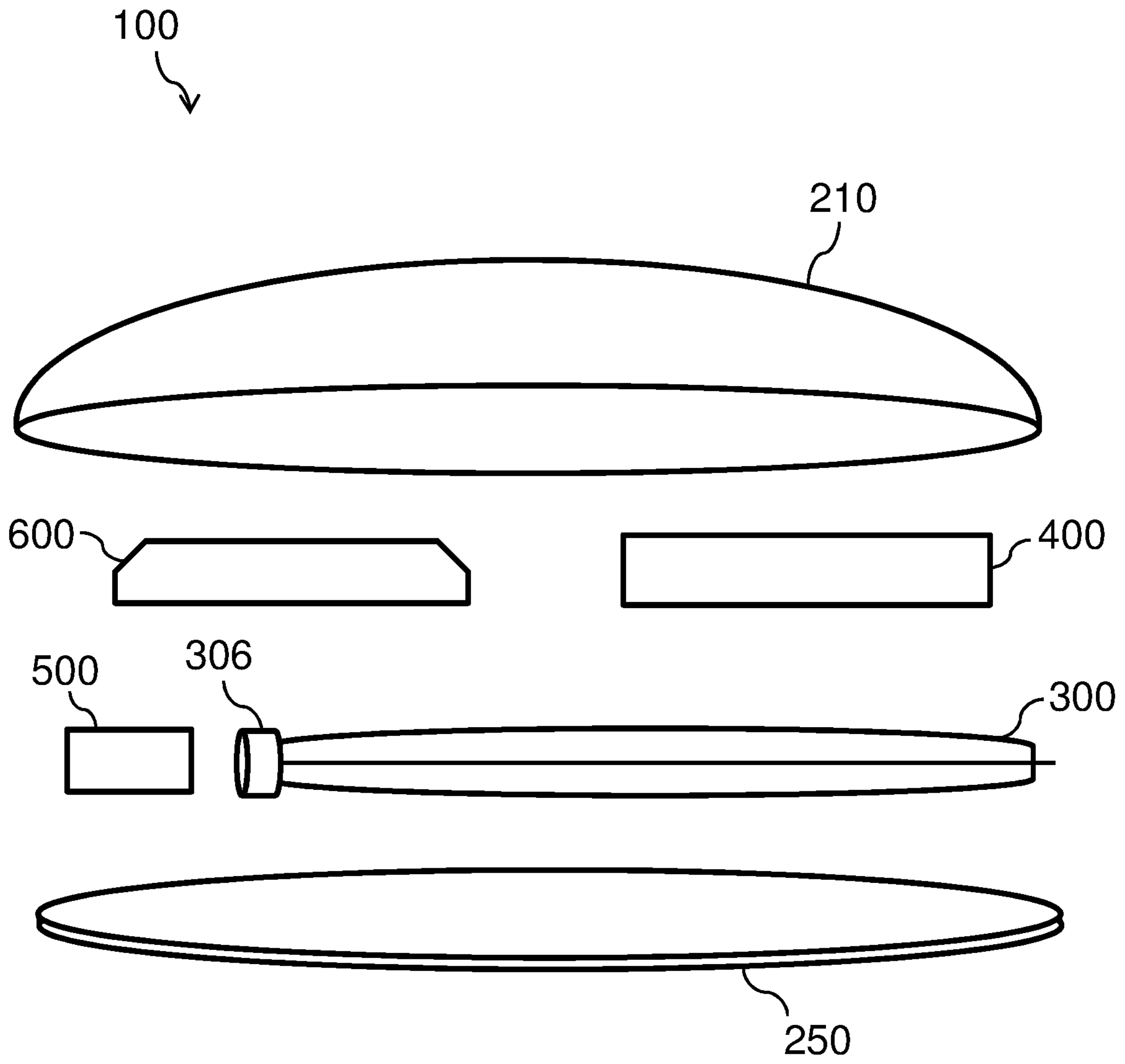
FIG. 2 illustrates an exploded view of the wearable injection device shown in FIG. 1, according to various embodiments of the present disclosure.

In FIG. 2, the components of injection device 100 have been simplified to provide a broad overview of the main elements of the device. In various embodiments, housing 200 of injection device 100 comprises flexible body 210. Flexible body 210 can be provided in a variety of shapes and materials. In various embodiments, flexible body 210 encloses many of the components of injection device 100.

In various embodiments, injection device 100 includes reservoir 300. Reservoir 300 comprises a flexible outer wall with an inner volume. In various embodiments, reservoir 300 contains a medicament, fluid, or gel that can be administered subcutaneously by injection device 100. Reservoir 300 can be provided in a variety of shapes, configurations, materials, and volumes. In various embodiments, reservoir 300 further comprises a port 306 in fluid communication with the inner volume. In various embodiments, reservoir 300 comprises an additional port that may be used for filling or refilling reservoir 300 with a medicament, fluid, or gel.

According to various embodiments of the present disclosure, injection device 100 comprises pump mechanism 400 configured to dispense a medicament from wearable injection device 100. In various embodiments, injection device 100 comprises injection mechanism 500 in fluid communication with the inner volume of the reservoir. Injection device 100 further comprises metering mechanism 600 configured to control a dosage of the medicament dispensed from the wearable injection device 100.

One advantage of the housings of the present disclosure is that they are flexible. When a patient uses injection device 100, housing 200 and flexible body 210 can be temporarily deformed without causing damage to the device or negatively affecting its function. Flexible body 210 can be provided in a variety of materials to achieve this advantage. For example, the material of flexible body 210 can have elastic properties to provide a flexible body and acceptable biocompatibility to be worn on the skin for a prolonged time.

Flexible body 210 can include a number of suitable materials. In various embodiments, flexible body 210 can comprise one of silicone polymer, polyurethane rubber, thermoplastic elastomer, polyvinyl chloride, or synthetic rubber, such as neoprene foam, styrene-butadiene rubber (SBR), styrene-chloroprene rubber (SCR) or chloroprene rubber (CR). In some embodiments, flexible body 210 can comprise polyethylene (PE), polypropylene (PP), polyvinylchloride (PVC), polyamide (PA), ethylene-vinyl-acetate (EVA), cycloolefinecopolymers (COC), cycloolefinpolymer (COP). Flexible body 210 can include multi-layer materials of different polymers. In various embodiments, flexible body 210 can comprise polymers and/or copolymers including, but not limited to, ethylene vinyl acetate, low-density polyethylene, polyolefin elastomers, or thermosetting elastomers, such as polypropylene elastomer.

The outer surface of flexible body 210 may also be covered with fabric to improve the comfort of wear. Flexible body 210 can have a water vapor transmission rate that can be beneficial to improve comfort of wearing the device and improve the biocompatibility between the material and the skin. In some embodiment, semipermeable membrane materials, such as GoreTex, can be used with flexible body 210.

In some embodiments, flexible body 210 can be provided as a combination of two or more materials. For example, flexible body 210 can be formed of a denser or stiffer and stronger material near the metering mechanism to enhance protection thereof, and can be formed of a less dense and more flexible material near its peripheral edge (identified, for example, as peripheral edge 211 in FIG. 3A). In this embodiment, the material at or near the peripheral edge 211 can provide a greater range of flexion and deformation so that it remains adhered to a patient's skin. In some embodiments, the denser material forms a pattern in the less dense material, such as a grid, array, spiral, or tessellate, which can provide sufficient impact protection while enhancing the deformability of flexible body 210 and reducing the weight of injection device 100.

Figure 3A:
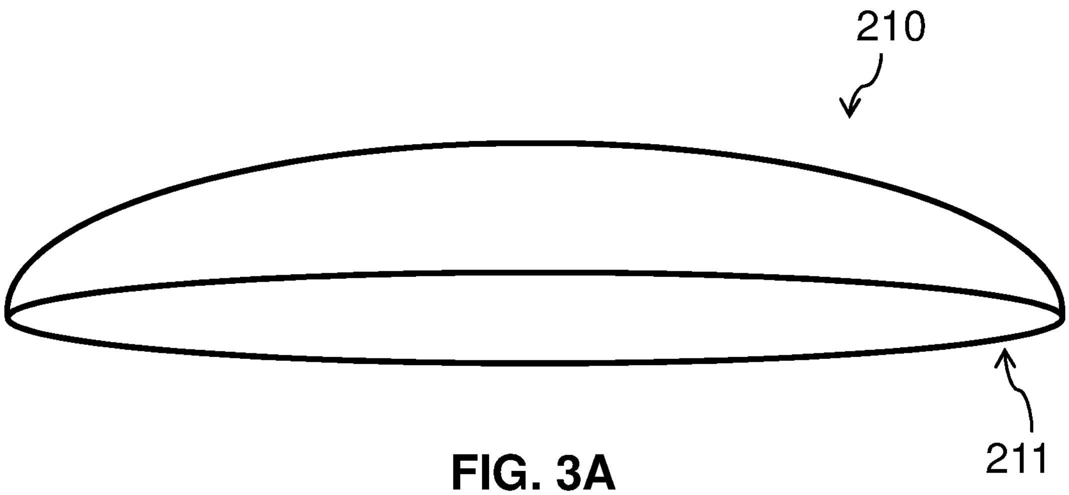
FIG. 3A illustrates the flexible body from FIG. 2, according to various embodiments of the present disclosure.
Figure 3B:
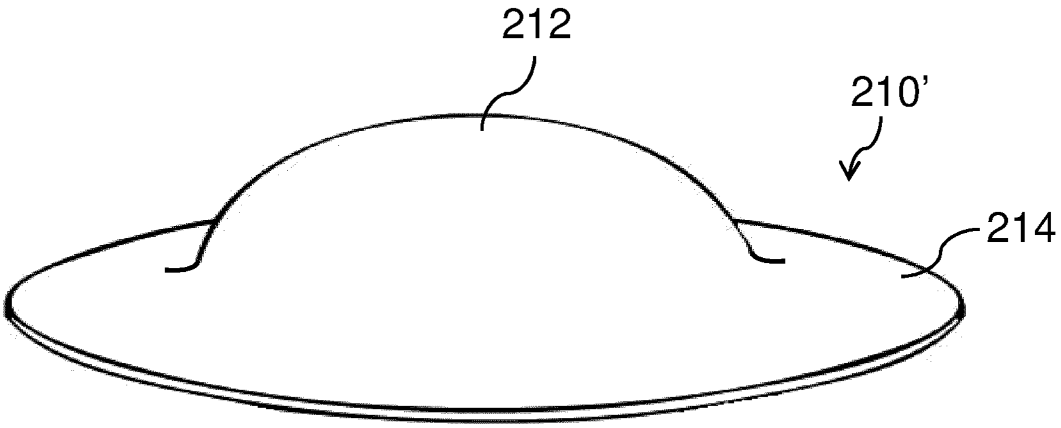
FIG. 3B illustrates a different embodiment of the flexible body from FIG. 2, according to various embodiments of the present disclosure.

As discussed above, flexible body 210 of injection device 100 can be provided in a variety of configurations and sizes. FIGS. 3A and 3B display different embodiments of flexible body 210. FIG. 3A illustrates flexible body 210 shown previously in FIG. 2, according to various embodiments of the present disclosure. Flexible body 210 comprises a partial ellipsoid shape and has a minimal height so that injection device 100 can have a low profile when adhered to a patient's skin.

In various embodiments, flexible body 210 comprises peripheral edge 211. While FIG. 3A depicts flexible body 210 with a concave, partial ellipsoid shape, flexible bodies of the present disclosure are not limited to such configurations. For example, flexible body 210 can be polygonal, prismatic, convex, partially convex, concave, partially concave, or a combination therebetween. In some embodiments, flexible body 210 mimics natural geometries, such as the shape of a turtle shell, clam shell, scallop shell, stingray, such as an ocellate river stingray, or portions or combinations thereof.

In some embodiments, flexible bodies of the present disclosure can include additional elements to improve adherence or streamline the profile of injection device 100. For example, FIG. 3B illustrates an alternative embodiment of the flexible body, according to various embodiments of the present disclosure. Flexible body 210' comprises dome 212 and flange 214. In various embodiments, flange 214 includes a curved, parabolic shape to reduce any edges or hard lines on flexible body 210'. Flange 214 also provides ample, flat surface area to adhere injection device 100 securely to a patient's skin. Flexible body 210' has a streamlined shape with a low profile that provides a minimalistic design that will be unobtrusive for patients.

In various embodiments, the surface of the flexible bodies of the present disclosure are provided in a variety of configurations. For example, flexible body 210, 210' can be provided in a range of colors. In some embodiments, flexible body 210, 210' are provided in a spectrum of skin tones so that wearable injection device 100 blends in a patient's skin. In some embodiments, flexible body 210, 210' has a variety of surface finishes and features to suit patient needs. For example, flexible body 210, 210' can have dimples that may improve a patient's grip on the device as they remove the device, for instance, to replace it. In further example, flexible body 210, 210' may have the same smoothness and/or texture as skin so that wearable injector 100 blends in with the skin and becomes less noticeable. In some embodiments, flexible body 210, 210' can be provided in colorful hues, patterns, and designs to suit a patient's style, or, for example, to make children more comfortable with the device.

In existing wearable injectors, the size of the reservoir influences the ultimate size of the injector itself. This is because existing reservoirs are typically cylindrically shaped, rigid cartridges. As the need for longer lasting patch pumps has risen, conventional reservoirs and batteries used in patch pumps grew in size to meet this need and resulted in pumps with increased weights and larger heights that extend further from the skin. The resulting injectors were more noticeable, heavier, bulkier, and protruded farther from the skin, increasing the likelihood of the injector getting caught on surfaces and dislodging. To allow for larger reservoir volumes without causing increases in the wearable injector height, the present disclosure provides reservoirs with flexible outer walls that are provided in a variety of configurations and sizes. The present disclosure further provides reservoirs whose shape can mirror the shape of the housing and nest within the housing.

Figure 4A:
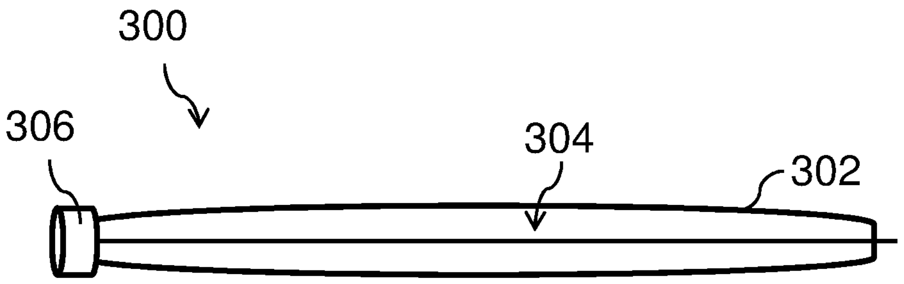
FIG. 4A illustrates a side view of the reservoir from FIG. 2, according to various embodiments of the present disclosure.
Figure 4B:
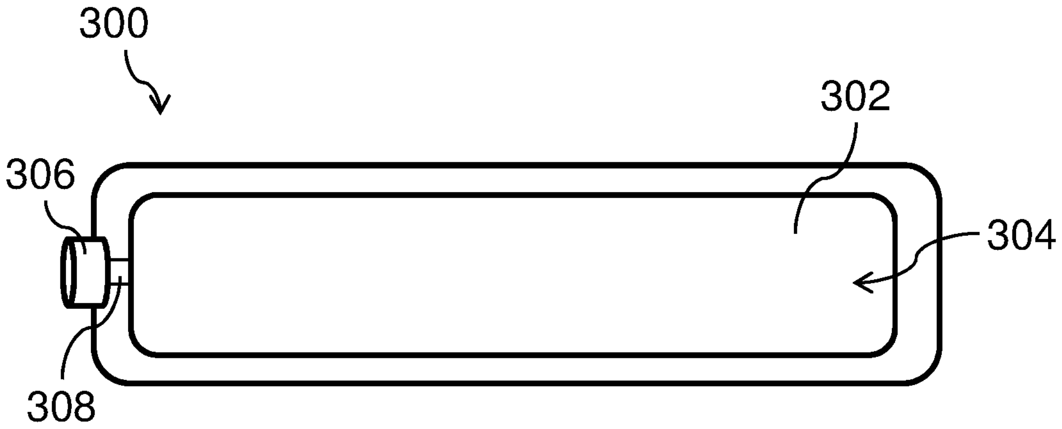
FIG. 4B illustrates a top view of the reservoir from FIG. 2, according to various embodiments of the present disclosure.
Figure 4C:
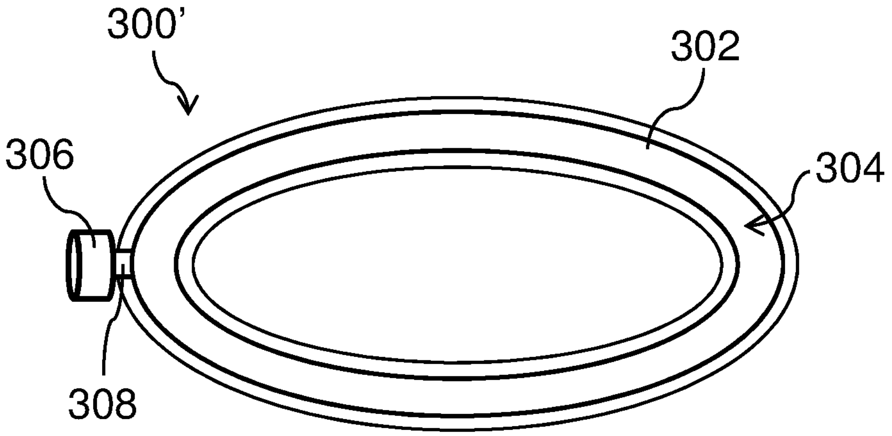
FIG. 4C illustrates a top view of another embodiment of a reservoir, according to various embodiments of the present disclosure.

FIGS. 4A-4C depict various reservoir embodiments of the present disclosure. Reservoir 300 from FIG. 2 is depicted in FIGS. 4A-4B. FIG. 4A illustrates a side view of reservoir 300 and FIG. 4B illustrates a top view of reservoir 300, according to various embodiments of the present disclosure. Reservoir 300 comprises flexible outer wall 302 and inner volume 304. Flexible outer wall can be provided in a variety of materials. For example, in some embodiments, flexible outer wall 302 comprises polymers like polyethylene (PE), polypropylene (PP), cycloolefinpolymer (COP), polyvinylchloride (PVC), polyamid (PA); copolymers like cycloolefin copolymer (COC), thermoplastics like various types of thermoplastic elastomer (TPE), silicones or various combinations therebetween.

Materials for the flexible reservoir 300 must comply with requirements for pharmaceutical use as primary container materials and must not affect the physico-chemical stability, purity, and sterility of the filled drug product. In some embodiments, reservoir 300 is protected by a separate, attached, or laminated flexible shield that is made of materials that are difficult to puncture, such as carbon fiber or Kevlar. In some embodiments, housing 200 is made of a material having a sufficient stiffness or rigidity to provide mechanical protection of reservoir 300 underneath.

Referring again to FIGS. 4A-4B, in various embodiments, reservoir 300 comprises at least one port 306. In addition, reservoir 300 includes channel 308 connecting port 306 with inner volume 304. In some embodiments, port 306 comprises a resealable membrane or valve (not pictured). In some embodiments, users can refill inner volume 304 of reservoir 300 by injecting medicament through port 306. In various embodiments, reservoir 300 comprises another port and channel dedicated for filling, while port 306 and channel 308 are dedicated to dispensing medicament.

Reservoirs of the present disclosure can be provided in a variety of configurations. FIG. 4C illustrates a top view of another embodiment of a reservoir, according to various embodiments of the present disclosure. Reservoir 300' is provided in an oval torus configuration and comprises the same elements as reservoir 300. Inner volume 304 of reservoir 300' is in the shape of an oval torus. Reservoirs of the present disclosure are provided in a variety of configurations, including, but not limited to, rectangular, circular, oval, or polygonal. In some embodiments, reservoirs of the present disclosure and can be provided in various symmetrical configurations, such as the infinity sign, or various asymmetrical configurations.

In various embodiments, inner volume 304 of reservoir 300, 300' is provided in a variety of volumes. In some embodiments, inner volume 304 is 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 35.0, 40.0, 45.0, 50.0 or more milliliters (mL). These values may be used to define discrete volumes, such as 5.0 mL, or ranges of volumes, such as 2.0-3.0 mL. In some embodiments, a maximum suitable volume may be up to 50 ml or more, where larger injections are required.

In various embodiments, due to the flexibility of reservoir 300, partial fill volumes may be used without jeopardizing the functional performance of the injection device. For example, a flexible reservoir capable of nominally holding 3 mL may only be filled to 2 mL to provide a flat reservoir. Further, the size of inner volume 304 can be adjusted depending on the density or viscosity of the medicament, the desired device operating time, or the available room within injection device 100.

In existing devices, rigid reservoir cartridges are present a number of challenges. For example, plungers used to push medicament toward the outlet of the rigid reservoirs make a tight seal with the inner walls of the reservoir. The maximum force required to overcome the static friction between the plunger and the reservoir wall is called the break-loose force. The energy required to advance plungers in existing devices with rigid reservoirs takes up considerable battery energy and space for the plunger to extend.

With the devices of the present disclosure, flexible reservoir 300 does not contain a plunger, and deformation of the flexible wall of the reservoir is sufficient to dispense medicament from the device. Because the devices of the present disclosure do not need to overcome a break-loose force, they can use smaller, more lightweight pumps that consume less energy and can use smaller batteries. Specifically, micro electromechanical system pumps (MEMS-micropumps) may be preferred for use with such devices, being small, precise in dosing and with low energy consumption. Further, the devices of the present disclosure do not need to accommodate space for the retraction and advancement of a plunger. For this reason, devices of the present disclosure can be smaller, lighter, and more flexible than existing devices.

In some embodiments, injection device 100 comprises multiple reservoirs. Multiple reservoirs can be implemented to optimize free space within injection device 100. In some embodiments, using two smaller reservoirs instead of one larger reservoir can optimize the space within the injection device and result in a device with a lower height and lower profile. In some embodiments, multiple reservoirs can increase the total volume of medicament within injection device 100 and extend its duration of use. This could reduce the frequency with which patients replace or refill the reservoirs. In some embodiments, multiple reservoirs can hold different medicaments for different patient needs. For example, with diabetes patients, one reservoir could be responsible for administering insulin at a basal rate while the other can be used for periodic bolus injections.

It will be noted that the term “flexible reservoir” or “flexible reservoirs” does not necessarily indicate that the entirety of the reservoir component is flexible. For example, port 306 may be rigid or semi-rigid so as to securely interlock with other elements of injection device 100, while outer wall 302 is flexible. However, in some embodiments, reservoir 300, 300' may be entirely flexible.

Figure 5A:
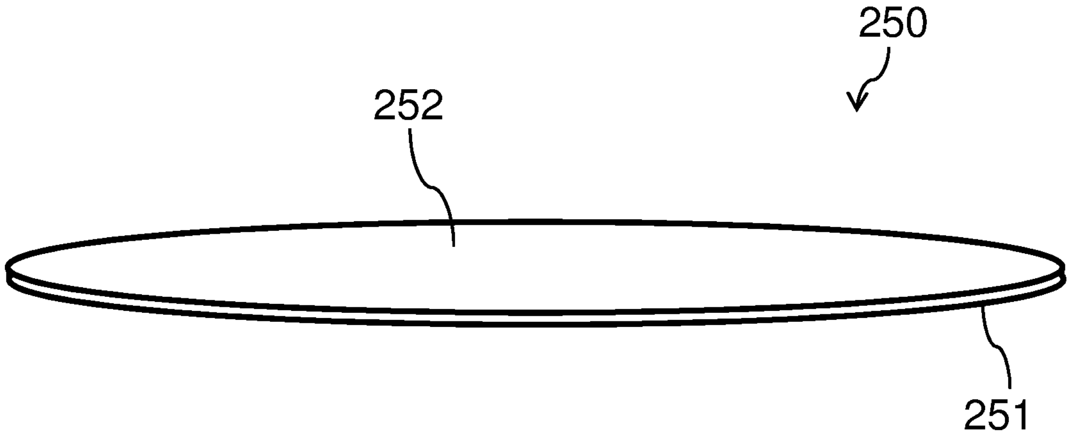
FIG. 5A illustrates an perspective view of the flexible base shown in FIG. 2, according to various embodiments of the present disclosure.

Another element of housing 200 is flexible base 250, which can be provided in a variety of configurations. FIG. 5A illustrates an isometric view of flexible base 250 shown in FIG. 2, according to various embodiments of the present disclosure. In various embodiments, flexible base 250 comprises flexible sheet 252 and peripheral edge 251. Flexible sheet 252 may comprise a variety of materials, including, but not limited to, polymers, copolymers, silicones, elastomers, rubbers, or combinations of these materials. The flexible sheet 252 may be able to stretch and twist along multiple axes. With such stretching and twisting, flexible sheet 252 can remain more securely adhered to the skin during body movements than existing stiff, planar surfaces that do not conform to the body during movement.

Figure 5B:
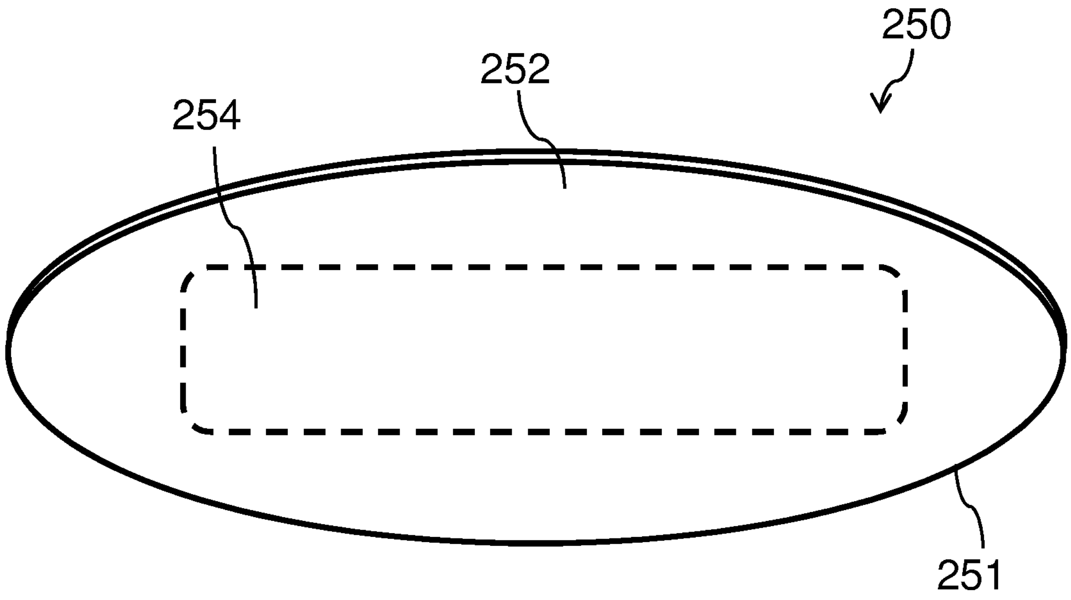
FIG. 5B illustrates a bottom view of the flexible base shown in FIG. 5A, according to various embodiments of the present disclosure.

FIG. 5B illustrates a bottom view of flexible base 250 shown in FIG. 5A, according to various embodiments of the present disclosure. Flexible base 250 further comprises adhesive 254. In various embodiments, adhesive 254 is an adhesive known in the art that enables secure bonding between flexible base 250 and the skin of a patient. In various embodiments, adhesive 254 covers all of one side of flexible sheet 252. In other embodiments, adhesive 254 covers a portion of flexible sheet 252. In some embodiments, adhesive 254 is positioned in an array or grid pattern across flexible sheet 252.

In various embodiments, peripheral edge 251 of flexible base 250 may align with peripheral edge 211 of flexible body 210. In some embodiments, housing 250 is sealed at the joining of peripheral edge 211 and peripheral edge 251. In some embodiments, portions of flexible body 210 lie against a patient's skin, for example, with the embodiment illustrated in FIG. 3B. In such embodiments, flexible base 250 takes up the area below dome 212 and forms a flat surface with flange 214.

Figure 6:
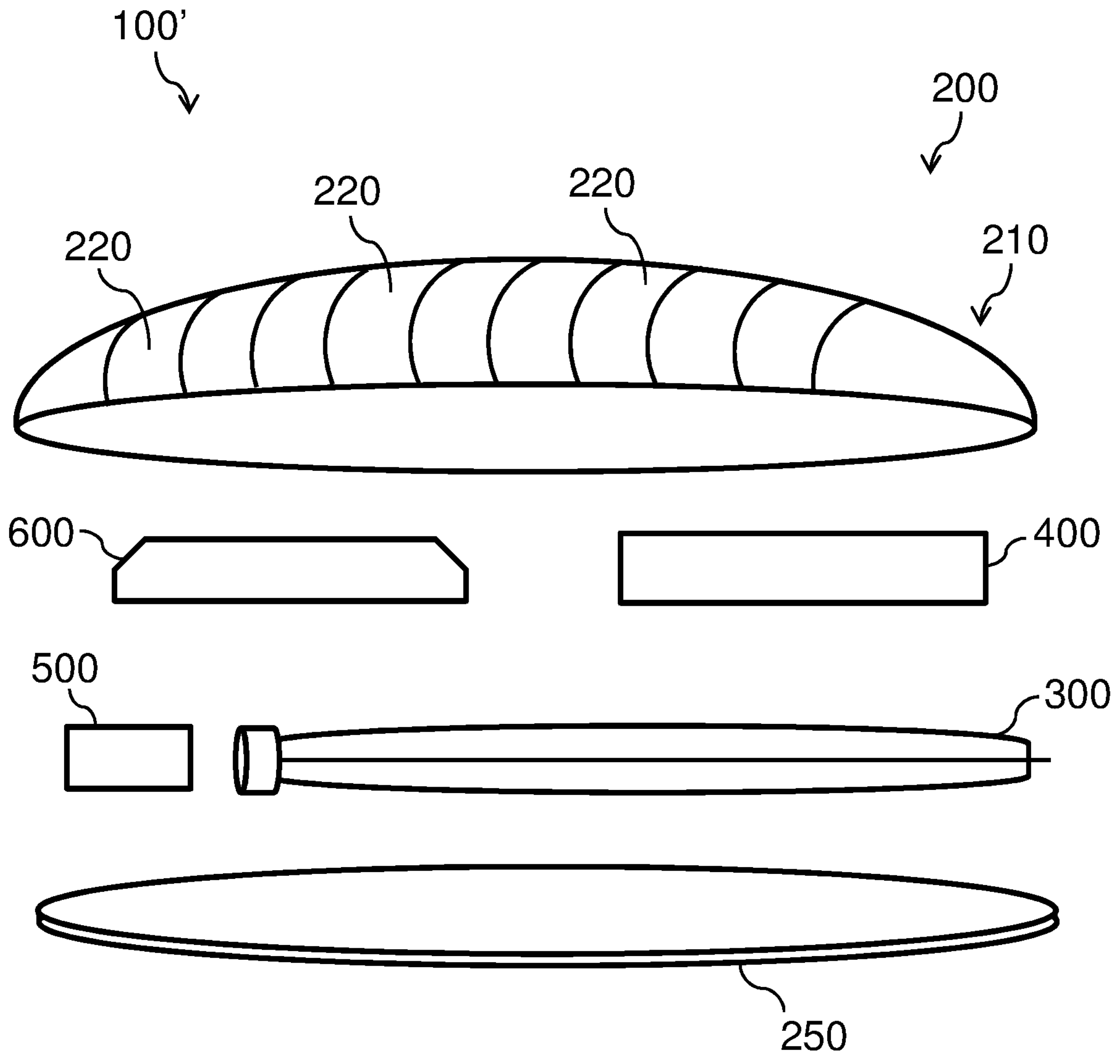
FIG. 6 illustrates another embodiment of a wearable injection device where the housing comprises multiple plates, according to various embodiments of the present disclosure.

In addition to providing flexible housing using flexible materials, embodiments of the present disclosure provide flexible housing using multiple plates. FIG. 6 illustrates injection device 100' where the housing comprises plates 220. In some embodiments, plates 220 are overlapping and are made of rigid or semi-rigid materials. In various embodiments, plates 220 are retractable. Similar to a lobster shell, housing flexibility can also be achieved when plates 220 can overlap at variable degrees and angles to enable bending, twisting, and torsion of flexible body 210.

Figure 7:
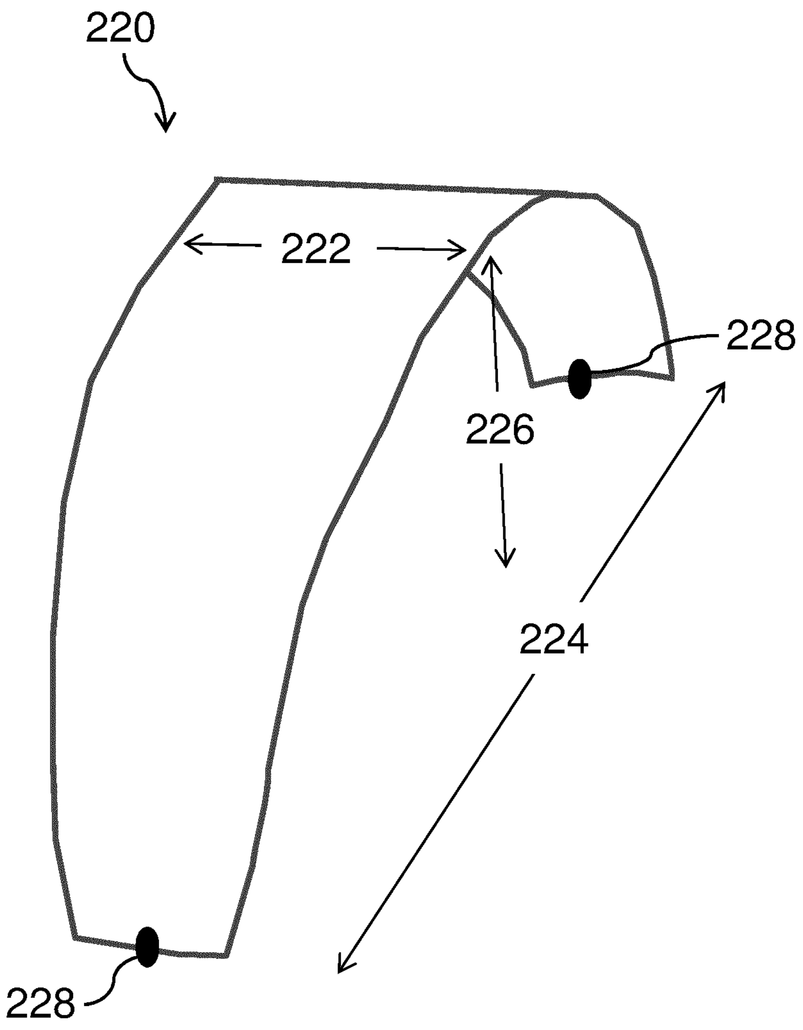
FIG. 7 illustrates one embodiment of a plate used in the housing of the wearable injection device shown in FIG. 6, according to various embodiments of the present disclosure.

FIG. 7 illustrates a perspective view of one plate 220 used in the housing of the wearable injection device, according to various embodiments of the present disclosure. In some embodiments, plate 220 comprises a width 222, length, 224, and height 226. Length 224 of plate 220 extends across the width of flexible body 210. To ensure plates 220 overlap and protect the inside of injection device 100', the sum of the widths 222 of each plate 220 is greater than the length of flexible body 210. In some embodiments, plates 220 have a varying degree of curvature and shape to ensure they conform around and adequately cover injection device 100'.

In some embodiments, plates 220 form arcs as depicted in FIG. 7. In some embodiments, plates 220 form narrow strips with tapered ends. In some embodiments, plates 220 comprise multiple flat segments and result in a polygonal flexible body 210. Material of construction for such plates are preferably plastic materials that have certain stiffness/rigidity as well as elastic properties. Suitable materials are polymers like polyethylene (PE), polypropylene (PP), polyvinylchloride (PVC), polyamide (PA), polyester like polyethylene-terephthalate (PET), polybutylene-terephthalate (PBT), polycarbonate (PC), polyestercarbonate (PEC), polystyrene (PS), acrylnitril-butadien-styrene copolymer (ABS); polyacetals like polyoxymethylene (POM), and the like. In some embodiments, each plate 220 is connected to at least one additional plate. In some embodiments, each plate 220 is connected by a thin, flexible substrate (not pictured). This substrate may be composed of a flexible material, such as a silicone polymer, silicone rubber, or thermoplastic elastomer. The substrate may be able to stretch and twist along multiple axes, but in a limited way, such that plates 220 always partially overlap and no gaps form between the plates.

Wearable injection devices with more rigid housings can break away from the patient during patient movement. For example, existing devices break away when the skin underneath the device is bent or deformed as a result of physical activity. Existing devices can also break away from the patient when the patient strikes a rigid structure, such as a doorframe. In various embodiments, the thin, flexible substrate provides a wearable injection device that conforms with and remains securely adhered to the skin during patient movement. In some embodiments, flexible body 210 comprises a rigid or semi-rigid ring around its peripheral edge 211. In such embodiments, points 228 on each plate 220 connect with the ring around peripheral edge 221.

In some embodiments, plates 220 comprise latches and hooks to prevent plates 220 from extending too far and resulting in gaps between plates 220 or openings in wearable injection device 100'. In some embodiments, plates 220 are arranged or positioned in a grid-like, array-like, or fish scale-like pattern. In such embodiments, length 224 of plate 220 is shorter than the width of flexible body 210. Much like chain mail, many, smaller plates 220 protect the inside of injection device 100' while allowing bending, twisting, and torsion of flexible body 210.

Referring back to FIGS. 2 and 6, wearable injection device 100, 100' further comprises pump mechanism 400 configured to dispense a medicament from the wearable injection device. In various embodiments, pump mechanism 400 comprises any of the available pump mechanisms know in the field. For example, pump mechanism 400 may comprise a microelectronic pump system. In various embodiments, pump mechanism 400 comprises a suction pump, a rotary piston pump, a dual piston pump, a membrane pump, or a micro-electromechanical system (MEMS) pump, among others. In some embodiments, pump mechanism 400 comprises MEMS pumps and sensors for their small form factors and precise dosing capabilities that require little energy. In this embodiment, smaller batteries can be used in the injection device that can result in smaller devices, lighter devices, and/or devices with lower profiles.

In some embodiments, wearable injection device 100, 100' further comprises injection mechanism 500 in fluid communication with inner volume 304 of reservoir 300, 300'. In various embodiments, injection mechanism 500 comprises any of the available injection mechanisms known in the field. For example, injection mechanism 500 may comprise a cannula and a cannula insertion system. In some embodiments, the cannula insertion system comprises an introducer needle, mechanisms to inject the needle, mechanisms to introduce the cannula, and mechanisms to retract the needle while leaving the cannula in place.

Injection mechanism 500 can inject medicament in a variety of modalities. In some embodiments, injection mechanism 500 administers the medicament subcutaneously. In some embodiments, injection mechanism 500 administers the medicament intramuscularly. In some embodiments, injection mechanism 500 administers the medicament intradermally. In some embodiments, injection mechanism 500 administers the medicament intravenously. In some embodiments, injection mechanism 500 includes a needle or cannula that can be inserted at various angles, including 90°, 75°, 60°, 45°, 25°, 15°, or 10° relative to the patient's skin. In some embodiments, the fluid path from the pump mechanism to the injection site may extend from the device as a tube line with attached needle to enable injection at an area of the skin that shall not be covered by an attached wearable injection device, like for intravenous injection.

In various embodiments, wearable injection device 100, 100' further comprises metering mechanism 600 configured to control a dosage of the medicament dispensed from wearable injection device 100, 100'. In various embodiments, metering mechanism 600 comprises any of the available metering mechanisms know in the field. For example, in some embodiments, metering mechanism 600 comprises a receiving means, a processor, sensors, and communication means connecting metering mechanism 600 with pump mechanism 400 and injection mechanism 500.

To enhance device flexibility and user comfort, in various embodiments, metering mechanism 600 further comprises a flexible circuit board. In some embodiments, metering mechanism 600 comprises a soft or flexible battery. In various embodiments, metering mechanism 600 further comprises an array of battery cells. An array of battery cells would allow designers more flexibility with where they can place individual batteries. This could aid in reducing the height or overall size of wearable injection device 100, 100'.

It should be understood that the specific plate 220 configurations of the present disclosure are exemplary and may be varied based on specific clinical goals. Accordingly, the material, size, shape, and quantity of plates 220 may be modified.

In various embodiments, the present disclosure provides methods of delivering medicament. The method comprises attaching a wearable injection device to a user. The method can comprise attaching any embodiment of wearable injection device provided in the present disclosure. For example, the method can comprise attaching injection device 100, 100' to a patient or user.

The next step in the method of delivering medicament comprises powering the wearable device, for example, injection device 100, 100'. In some embodiments, the wearable injection device can be powered with a physical button on the device. Alternatively, in some embodiments, the wearable injection device can be powered using an external source, for example using an external remote or an application loaded onto an electronic device.

In embodiments where the device is powered using an external source, the method of delivering medicament comprises sending a signal by wireless means, such as radio frequency, near-field communication (NFC), or Bluetooth. In various embodiments, wireless signal transmission makes delivering medicament easier during dynamic patient states.

Next, the method of delivering medicament comprises sending a signal to the metering mechanism. As with powering on the device, sending a signal to the metering mechanism can comprise pressing a button on a device or wirelessly activating the metering system using an external source. In various embodiments, the metering mechanism dispenses medicament from the reservoir. In some embodiments, the metering mechanism activates the pump mechanism to withdraw medicament from the reservoir. Next, the medicament travels through a connecting fluid path from the reservoir to the pump system and then to the injection system. In various embodiments, pump system dispenses medicament into the cannula.

The following step of the method of delivering medicament comprises dispensing a medicament at a programmable dosage and frequency. In this step, medicament passes through the cannula or needle into a desired injection site. The wearable injection device can be programmed to regularly and continuously or continually dispense a drug. The device may provide continuous basal doses and/or intermittent bolus doses. Programming the device thus may enable a user to deliver specific drug dosing profiles over a time period.

Programming the device can also enable a user to automate adjustments to dose profiles. For example, a user can program the device to adjust a dose profile in reaction to input from external sensors, such as from continuous blood glucose measurement (CGM) sensors. This is useful, for example, when administering basal insulin to a diabetes patient. Additionally, in some embodiments, a patient or user can dispense bolus drug injections at various times during the day.

The methods of delivering medicament of the present disclosure further comprise bending or compressing the wearable injection device without permanently affecting the performance and function of the wearable injection device. This step is enabled by the flexible elements, such as flexible reservoir 300, 300', flexible body 210, 210', and flexible elements of metering mechanism 600 described above in connection with injection device 100, 100'.

In various embodiments, the method of delivering medicament further comprises replacing the entire device to replenish the medicament. In these embodiments, the entire wearable injection device is a disposable device. In some embodiments, the method of delivering medicament further comprises replacing the reservoir to replenish the medicament. Users, such as patients, doctors, or medical professionals, can be authorized to replace the entire device or just the reservoir 300, 300' when the volume of medicament runs low, runs out, or treatment time exceeds the allowed in-use time of the medicament. In some embodiments, users can replace the entire reservoir. In various embodiments, users can refill the reservoir with medicament.

The terms “drug” or “medicament” are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient (“API”), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasm ids, or liposomes. Mixtures of one or more drugs are also contemplated.

The drug or medicament may be contained in a primary package or “drug container” adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 3 years. Storage may occur at room temperature (e.g., about 20° C.), or refrigerated temperatures (e.g., from about +2° C. to about 8° C.).

In some embodiments, the drug container is flexible and can have multiple flexible chambers inside of it to dispense more than one drug at the same time. For example, in some embodiments, the device can include in some instances, the drug container may be or may include a dual-chamber vessel configured to store two or more components of the pharmaceutical formulation to-be-administered (e.g., an API and a diluent, or two different drugs) separately, one in each chamber. In such instances, the two chambers of the dual-chamber container may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, pain, blood pressure disorders, macular degeneration, inflammation, hay fever, atherosclerosis and/or rheumatoid arthritis. Examples of APIs and drugs are those as described in handbooks such as Rote Liste 2019 for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrome.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

In one embodiment of the present disclosure, a wearable injection device includes a housing comprising a flexible body and a reservoir. The reservoir includes a flexible outer wall with an inner volume and at least one port in fluid communication with the inner volume. In some embodiments, the at least one port of the wearable injection device includes a resealable membrane or valve. The wearable injection device further includes a pump mechanism configured to dispense a medicament from the wearable injection device. The wearable injection device further includes an injection mechanism in fluid communication with the inner volume of the reservoir and a metering mechanism configured to control a dosage of the medicament dispensed from the wearable injection device.

In some embodiments, the medicament of the wearable injection device is insulin, comprising one of a human insulin, a human insulin analogue or derivative, a glucagon-like peptide (GLP-1), a GLP-1 analogue, a GLP-1 receptor agonists, a GLP-1 analogue or derivative, a dipeptidyl peptidase-4 (DPP4) inhibitor, a pharmaceutically acceptable DPP4 salt, a DPP4 solvate, or any mixture thereof.

In some embodiments, the flexible body of the wearable injection device includes plates. In some embodiments, the plates of the flexible body are made of a rigid or a semi-rigid material. In some embodiments, the plates of the flexible body are arranged in fish scale-like pattern. In some embodiments, the plates of the flexible body are partially overlapping. In some embodiments, the plates are connected to at least one additional plate. In some embodiments, the plates are connected a flexible substrate.

In some embodiments, the flexible body of the housing includes one of silicone, polyurethane rubber, thermoplastic elastomer, or neoprene foam. In some embodiments, the housing further includes a flexible base. In some embodiments, the flexible base includes a flexible sheet and an adhesive coating on at least a portion of the flexible sheet.

In some embodiments, the injection mechanism of the wearable injection device includes a cannula and a cannula insertion system. In some embodiments, the metering mechanism of the wearable injection device includes a receiving means, a processor, sensors, and communication means connecting the metering mechanism with the pump mechanism and the injection mechanism. In some embodiments, the metering mechanism of the wearable injection device further includes a flexible circuit board and a soft or flexible battery.

In one embodiment of the present disclosure, a method of delivering medicament includes attaching a wearable injection device to a user, powering the wearable device, sending a signal to the metering mechanism, and dispensing a medicament at a programmable dosage and frequency. In some embodiments, sending a signal to the metering mechanism includes touching the wearable injection device or sending a signal through a separate device by wireless means, such as radio frequency, near-field communication, or Bluetooth.

The wearable injection device of the method of delivering medicament includes a housing including a flexible body and a reservoir. The reservoir includes a flexible outer wall with an inner volume and at least one port in fluid communication with the inner volume. The wearable injection device of the method of delivering medicament further includes a pump mechanism configured to dispense a medicament from the wearable injection device and an injection mechanism in fluid communication with the inner volume of the reservoir. The wearable injection device of the method of delivering medicament further includes a metering mechanism configured to control a dosage of the medicament dispensed from the wearable injection device.

In some embodiments, the method of delivering medicament includes bending or compressing the wearable injection device without permanently affecting the performance and function of the wearable injection device. In some embodiments, the method of delivering medicament further includes replacing or refilling the reservoir to replenish the medicament.

In some embodiments, dispensing the medicament includes dispensing a diabetes medication, comprising one of a human insulin, a human insulin analogue or derivative, a glucagon-like peptide (GLP-1), a GLP-1 analogue, a GLP-1 receptor agonists, a GLP-1 analogue or derivative, a dipeptidyl peptidase-4 (DPP4) inhibitor, a pharmaceutically acceptable DPP4 salt, a DPP4 solvate, or any mixture thereof.

In one embodiment of the present disclosure, a reservoir used in an injection device includes a flexible outer wall, an inner volume, at least one port, and a channel connecting the at least one port with the inner volume. In some embodiments, the flexible outer wall of the reservoir used in an injection device includes one of a polymer or silicone. In some embodiments, the at least one port of the reservoir used in an injection device includes a resealable membrane or valve.

Generally, the wearable injection devices of the present disclosure provide significant benefits over traditional injection devices and older methods such as self-administering shots of medicament. The flexible elements disclosed herein provide wearable injection devices with low weights, small heights, low profiles, and streamlined, flexible cases that can conform with the patient's skin and withstand impact without experiencing adverse performance effects or tearing away from the patient. Additional embodiments, configurations, uses, and methods of the present disclosure will be obvious to a person of ordinary skill in the art.

The invention claimed is:

1. A wearable injection device (100') comprising:
- a housing (200) comprising a flexible body (210), comprising:
  - a flexible base; and
  - a flexible top housing formed of a group of partially overlapping plates (220);
- a reservoir (300, 300') comprising:
  - a flexible outer wall (302) with an inner volume (304); and
  - at least one port (306) in fluid communication with the inner volume (304);

- a pump mechanism (400) configured to dispense a medicament from the wearable injection device (100');
- an injection mechanism (500) in fluid communication with the inner volume (304) of the reservoir (300, 300'); and
- a metering mechanism (600) configured to control a dosage of the medicament dispensed from the wearable injection device (100').

2. The wearable injection device of claim 1, wherein the medicament is diabetes medication, comprising one of a human insulin, a human insulin analogue or derivative, a glucagon-like peptide (GLP-1), a GLP-1 analogue, a GLP-1 receptor agonists, a GLP-1 analogue or derivative, a dipeptidyl peptidase-4 (DPP4) inhibitor, a pharmaceutically acceptable DPP4 salt, a DPP4 solvate, or any mixture thereof.

3. The wearable injection device of claim 1, wherein each of the plates (220) is flexibly connected to at least one other plate (220), to a flexible substrate, or to the flexible base (250) of the housing (200).

4. The wearable injection device of claim 1, wherein the plates (220) are made of a rigid or a semi-rigid material.

5. The wearable injection device of claim 3, wherein the plates (220) are arranged in fish scale-like pattern.

6. The wearable injection device of claim 1, wherein the flexible body (210) of the housing (200) comprises one of silicone, polyurethane rubber, thermoplastic elastomer, or neoprene foam.

7. The wearable injection device of claim 1, wherein the flexible base (250) comprises a flexible sheet (252) and an adhesive (254) coating on at least a portion of the flexible sheet (252).

8. The wearable injection device of claim 1, wherein the injection mechanism (500) comprises a cannula and a cannula insertion system.

9. The wearable injection device of claim 1, wherein the metering mechanism (600) further comprises:
- a receiving means;
- a processor;
- sensors; and
- communication means connecting the metering mechanism with the pump mechanism and the injection mechanism.

10. The wearable injection device of claim 1, wherein the metering mechanism (600) further comprises a flexible circuit board and a soft or flexible battery.

11. A method of delivering medicament comprising:
- attaching a wearable injection device to a user, the wearable injection device comprising:
- a housing (200) comprising a flexible body (210), comprising:
- a flexible base; and
- a flexible top housing formed of a group of partially overlapping plates (220);
- a reservoir (300, 300') comprising:
- a flexible outer wall (302) with an inner volume (304); and
- at least one port (306) in fluid communication with the inner volume (304);
- a pump mechanism (400) configured to dispense a medicament from the wearable injection device (100');
- an injection mechanism (500) in fluid communication with the inner volume (304) of the reservoir (300, 300'); and
- a metering mechanism (600) configured to control a dosage of the medicament dispensed from the wearable injection device (100');

powering the wearable injection device (100');
sending a signal to the metering mechanism (600); and
dispensing a medicament at a programmable dosage and frequency.

12. The method of claim 11, wherein the method further comprises bending or compressing the wearable injection device (100') without permanently affecting the performance and function of the wearable injection device (100').

13. The method of claim 11, wherein sending a signal to the metering mechanism (600) comprises touching the wearable injection device (100') or sending a signal through a separate device by wireless means, such as radio frequency, near-field communication, or Bluetooth.

14. The method of claim 11, wherein dispensing the medicament comprises dispensing diabetes medication, comprising one of a human insulin, a human insulin analogue or derivative, a glucagon-like peptide (GLP-1), a GLP-1 analogue, a GLP-1 receptor agonists, a GLP-1 analogue or derivative, a dipeptidyl peptidase-4 (DPP4) inhibitor, a pharmaceutically acceptable DPP4 salt, a DPP4 solvate, or any mixture thereof.

* * * * *